United States Patent
Zhang et al.

(10) Patent No.: US 11,773,718 B2
(45) Date of Patent: Oct. 3, 2023

(54) FORMATION FLUID SAMPLING METHODS AND SYSTEMS

(71) Applicant: HALLIBURTON ENERGY SERVICES, INC., Houston, TX (US)

(72) Inventors: Lizheng Zhang, Humble, TX (US); Nestor Rodriguez, Shenandoah, TX (US); William Wade Samec, Katy, TX (US); James Masino, Houston, TX (US); Burkay Donderici, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 616 days.

(21) Appl. No.: 15/115,639

(22) PCT Filed: Mar. 7, 2014

(86) PCT No.: PCT/US2014/022064
§ 371 (c)(1),
(2) Date: Jul. 29, 2016

(87) PCT Pub. No.: WO2015/134043
PCT Pub. Date: Sep. 11, 2015

(65) Prior Publication Data
US 2017/0167255 A1    Jun. 15, 2017

(51) Int. Cl.
*G01N 33/00*    (2006.01)
*G01N 33/24*    (2006.01)
(Continued)

(52) U.S. Cl.
CPC .......... *E21B 49/0875* (2020.05); *E21B 47/06* (2013.01); *E21B 47/07* (2020.05);
(Continued)

(58) Field of Classification Search
CPC .............................. G01N 1/14; G01N 1/2035
See application file for complete search history.

(56) References Cited

U.S. PATENT DOCUMENTS 5,289,875 A    3/1994  Stokley et al.
7,210,343 B2   5/2007  Shammai et al.
(Continued)

FOREIGN PATENT DOCUMENTS

WO    2015/134043    9/2015

OTHER PUBLICATIONS

PCT International Search Report and Written Opinion, dated Dec. 5, 2014, Appl No. PCT/US2014/022064, "Formation Fluid Sampling Methods and Systems," Filed Mar. 7, 2014, 15 pgs.

*Primary Examiner* — Brian R Gordon
*Assistant Examiner* — Dwan A Gerido
(74) *Attorney, Agent, or Firm* — John Wustenberg; Parker Justiss, P.C.

(57) ABSTRACT

Disclosed herein are methods and system for formation fluid sampling. In at least some embodiments, the method includes pumping formation fluid from a public flow line of a downhole tool via a private flow line into a detachable sample chamber. The method also includes isolating the private flow line from the public flow line. The method also includes collecting measurements of the formation fluid in the private flow line. The method also includes associating the measurements with the detachable sample chamber.

11 Claims, 7 Drawing Sheets

(51) Int. Cl.
 *G01N 1/20* (2006.01)
 *G01N 1/14* (2006.01)
 *E21B 49/08* (2006.01)
 *E21B 47/06* (2012.01)
 *G01N 1/12* (2006.01)
 *G01N 1/16* (2006.01)
 *E21B 47/07* (2012.01)

(52) U.S. Cl.
 CPC .......... *E21B 49/081* (2013.01); *E21B 49/084* (2013.01); *G01N 1/12* (2013.01); *G01N 1/14* (2013.01); *G01N 1/16* (2013.01); *G01N 1/2035* (2013.01); *G01N 33/0044* (2013.01); *G01N 33/24* (2013.01); *G01N 2001/205* (2013.01); *G01N 2001/2071* (2013.01)

(56) References Cited

U.S. PATENT DOCUMENTS

| | | | |
|---|---|---|---|
| 7,669,469 B2 | 5/2010 | Shammai et al. | |
| 7,671,983 B2 | 5/2010 | Shammai et al. | |
| 8,210,260 B2 | 7/2012 | Milkovisch et al. | |
| 2002/0194906 A1* | 12/2002 | Goodwin | E21B 49/08 73/152.46 |
| 2003/0033866 A1 | 2/2003 | Diakonov et al. | |
| 2005/0028974 A1 | 2/2005 | Moody | |
| 2006/0131376 A1 | 6/2006 | Bargach et al. | |
| 2008/0066904 A1* | 3/2008 | Van Hal | E21B 36/008 166/250.1 |
| 2008/0087470 A1* | 4/2008 | Villareal | E21B 17/16 175/50 |
| 2010/0170717 A1 | 7/2010 | Villareal | |
| 2011/0093200 A1* | 4/2011 | Hsu | E21B 47/10 702/8 |
| 2011/0132609 A1 | 6/2011 | Van Hal et al. | |
| 2013/0025855 A1* | 1/2013 | Glattetre | E21B 49/08 166/264 |
| 2014/0260586 A1* | 9/2014 | Van Hal | E21B 49/082 73/152.07 |
| 2015/0159484 A1* | 6/2015 | Dumont | E21B 49/088 166/250.02 |

* cited by examiner

FORMATION FLUID SAMPLING METHODS AND SYSTEMS

BACKGROUND

During oil and gas exploration, many types of information are collected and analyzed. The information is used to determine the quantity and quality of hydrocarbons in a reservoir, and to develop or modify strategies for hydrocarbon production. One technique for collecting relevant information involves obtaining and analyzing fluid samples from a reservoir of interest. Providing accurate fluid sample analysis is challenging due to: 1) limited fluid sample analysis options in the downhole environment; and 2) collected samples undergo changes if transported to earth's surface where more analysis options are available. Efforts to improve such fluid sampling and analysis techniques are ongoing.

BRIEF DESCRIPTION OF THE DRAWINGS

Accordingly, there are disclosed herein formation fluid sampling methods and systems. In the drawings.

It should be understood, however, that the specific embodiments given in the drawings and detailed description thereto do not limit the disclosure. On the contrary, they provide the foundation for one of ordinary skill to discern the alternative forms. equivalents, and modifications that are encompassed together with one or more of the given embodiments in the scope of the appended claims.

DETAILED DESCRIPTION

Disclosed herein are formation fluid sampling methods and systems. In at least some embodiments, formation fluid is sampled by pumping formation fluid from a public flow line of a downhole tool via a private flow line into a detachable sample chamber, where the private flow line is isolated from the public flow line. While and/or after filling the detachable sample chamber, measurements of formation fluid in the private flow line are collected. These measurements are associated with the detachable sample chamber, and can be collected by a set of sensors integrated with the private flow line or otherwise in situ with the private flow line. The collection of measurements along the private flow line enables chamber-specific monitoring without increasing the complexity of a detachable sample chamber since fewer or no sensors need be included with the detachable sample chamber.

In at least some embodiments, formation fluid collected in a detachable sample chamber is further analyzed at earth's surface by removing the detachable sample chamber from the downhole tool and transporting it to a formation fluid analysis station or laboratory. Before removal from the downhole tool, the detachable sample chamber from the downhole tool is sealed to isolate it from the private flow line. Further, measurements collected while the downhole tool was below earth's surface may be communicated to the formation fluid analysis station for use in the analysis. As an example, such measurements may include temperature, pressure, dielectric strength, fluid density, resistivity, phase changes, $H_2S$ concentrations, and $H_2S$ absorptions rates. If is multiple detachable sample chambers are used, the measurements may be tagged with a unique identifier to associate the measurements with a respective detachable sample chamber.

A formation fluid sampling controller may direct various operations. For example, the controller may initiate operations of a pre-fill stage, in which a pump cycles formation fluid through the public flow line until public flow line sensors indicate a fluid quality threshold is reached. In at least some embodiments, the fluid quality threshold corresponds to threshold values for fluid density, dielectric strength, and resistivity. Thereafter, the controller may initiate fill stage operations for a detachable sample chamber by opening an isolation valve between the public flow line and a private flow line associated with the detachable sample chamber. Once the fill stage operations are complete, the controller directs the isolation valve to close. Thereafter, transport stage operations are initiated to transport one or more filled detachable sample chambers to earth's surface. During the fill stage and/or transport stage operations, measurements along the private flow line are collected. As needed, the controller may initiate replacement sample operations in response to these measurements indicating a problem such as a leak in the isolation valve or detachable sample chamber, contamination, and/or an unsuitable sample. The replacement sample operations may involve the same detachable sample chamber or another detachable sample chamber.

Figure 1:
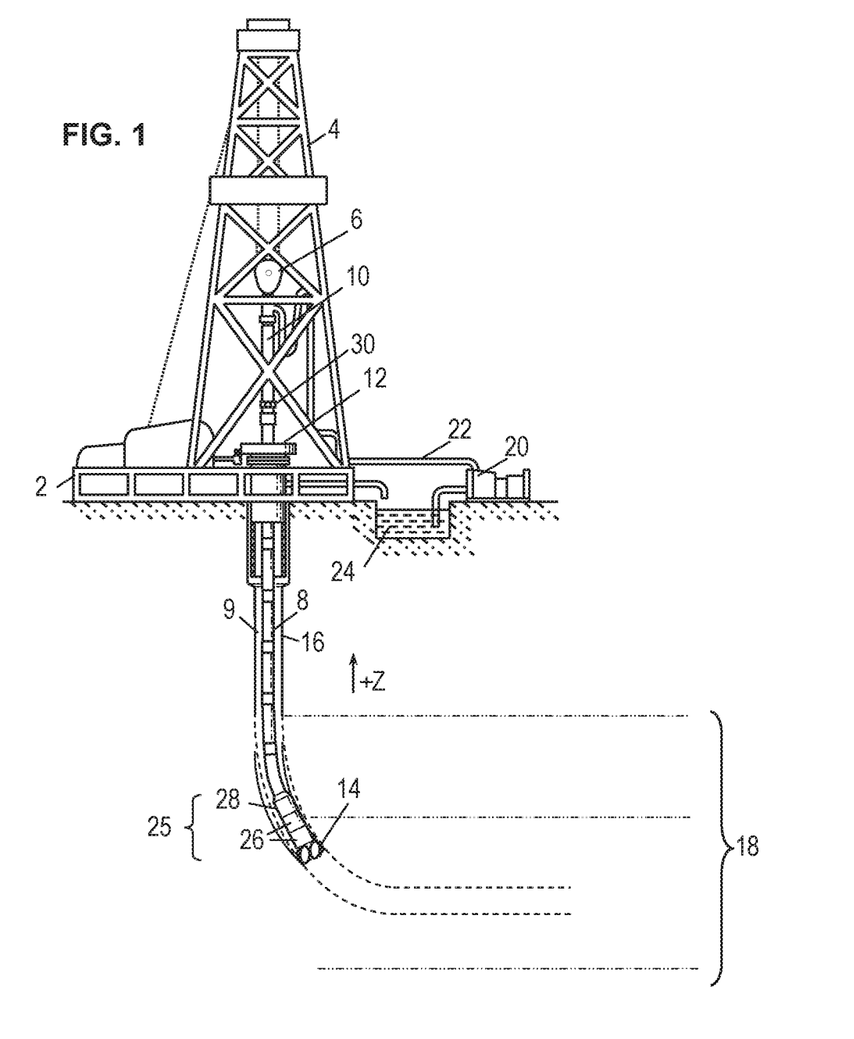
FIG. 1 shows an illustrative logging-while-drilling tool environment.

The disclosed fluid sampling embodiments can be best appreciated in the context of logging-while-drilling (LWD) environments and wireline logging environments. FIG. 1 shows an illustrative LWD environment. In FIG. 1, a drilling platform 2 supports a derrick 4 having a traveling block 6 for raising and lowering a drill string 8. A drill string kelly 10 supports the rest of the drill string 8 as it is lowered through a rotary table 12. The rotary table 12 rotates the drill string 8, thereby turning a drill bit 14. As bit 14 rotates, it creates a borehole 16 that passes through various formations 18. A pump 20 circulates drilling fluid through a feed pipe 22 to kelly 10, downhole through the interior of drill string 8, through orifices in drill bit 14, back to the surface via the annulus 9 around drill string 8, and into a retention pit 24. The drilling fluid transports cuttings from the borehole 16 into the pit 24 and aids in maintaining the integrity of the borehole 16.

The drill bit 14 is just one piece of an open-hole LWD assembly that includes one or more drill collars 26 and downhole tool 28. Drill collars 26 are thick-walled steel pipe sections that provide weight and rigidity for the drilling process. The downhole tool 28 (which may be built into the drill collars) gathers measurements of various drilling and/or collect fluid samples as described herein.

Figure 2:
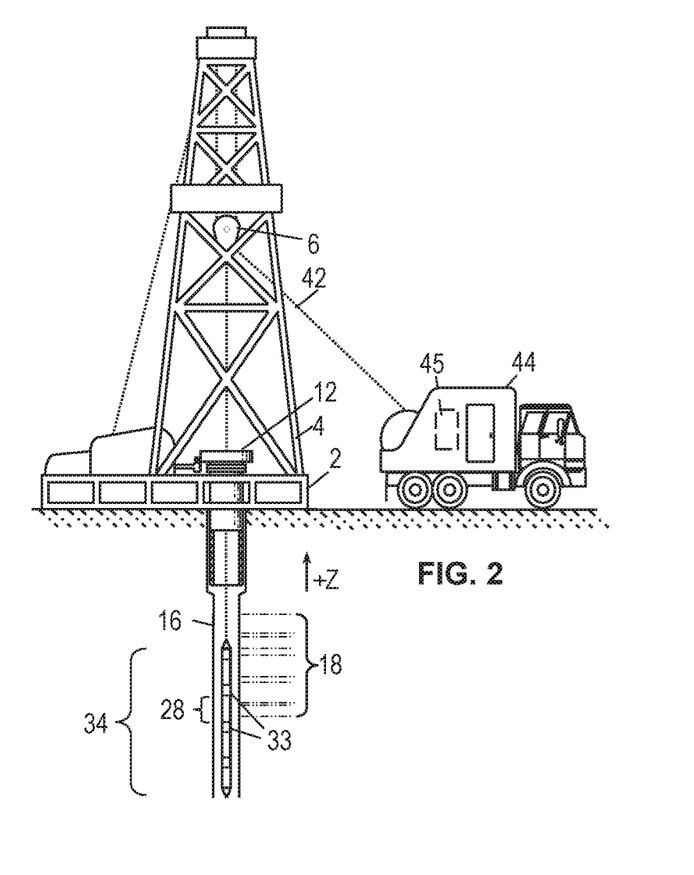
FIG. 2 shows an illustrative wireline tool environment.

At various times during the drilling process, the drill string 8 shown in FIG. 1 may be removed from the borehole 16. In at least some embodiments, the removal process of the drill string 8 can be paused so that downhole tool 28 can collect fluid samples as described herein. Such fluid samples can also be collected after the drill string 8 is removed using a wireline tool string 34 as is shown in FIG. 2. In at least some embodiments, the wireline tool string 34 corresponds to an assembly of wireline tools suspended in borehole 16 by a cable 42 having conductors for transporting power to the tools and telemetry from the tools to the surface. It should be noted that various types of formation property sensors can be included with the wireline tool string 34. As shown, the illustrative wireline tool string 34 includes downhole tool 28, which may collect formation fluid samples as described herein. The downhole tool 28 may be coupled to other modules of the wireline tool string 34 by one or more adaptors 33.

In FIG. 2, a wireline tool facility 44 collects measurements from the downhole tool 28, and includes computing facilities 45 for managing wireline operations, acquiring and storing the measurements gathered by the wireline tool string 34, and processing or otherwise analyzing the measurements.

FIG. 3A-3D show an illustrative formation fluid sampling system 100 during various stages of a sampling process. In accordance with at least some embodiments, the system 100 comprises a fluid sampling assembly 101 that may be, for example, part of the downhole tool 28. The system 100 also may include auxiliary components (not shown) that are part of the downhole tool 28, such as a probe, seals, and/or a positioning mechanism to ensure the sampling system 100 is able to receive fluid from a formation (through suitable contact with the borehole wall) rather than borehole fluid.

As shown, the fluid sampling assembly 101 includes a public flow line 102 with valves 103 and 105. The valves 103 and 105 are actuated using respective control signals, CTR_PB1 and CTR_PB2. The fluid sampling assembly 101 also includes a pump 106 along the public flow line 102 to draw fluid into and to direct fluid out of the public flow line 102. Public flow line sensors 104 are also positioned along the public flow line 102 and operate to at least determine whether the quality of formation fluid in the public flow line 102 is higher than a threshold level. This threshold level at least distinguishes between formation fluid and borehole fluid. For example, chemical analysis, particle size analysis, or other analysis may be employed to determine whether the public flow line 102 contains formation fluid, borehole fluid, or both. The threshold level also may define a level of desired formation fluid purity, where borehole fluid is a detectable contaminant that is acceptable up to predetermined trace levels.

The fluid sampling assembly 101 also includes a plurality of private flow lines 107A-107N that are selectively isolated from the public flow line 102 using respective isolation valves 108A-108N, each actuated by a separate control signal CTR_PV1 to CTR_PVN. Each of the private flow lines 107A-107N includes respective private flow line sensors 110A-110N. Examples of private flow line sensors 110A-110N include temperature sensors, pressure sensors, density sensors, dielectric strength sensors, chemical presence/concentration sensors, electromagnetic sensors, resistivity sensors, acoustic sensors, and/or $H_2S$ sensors.

In at least some embodiments, one or more of the private flow line sensors 110A-110N correspond to a pressure transducer sensor fabricated using a strain gauge, a temperature sensor, and a pressure vessel. More specifically, the gauge and sensor are attached to the vessel and the two outputs are used to characterize the vessel's response to pressure. With this technique, a private flow line or a sample chamber becomes a pressure transducer sensor. If the pressure transducer sensor includes the sample chamber, corresponding pressure measurements can be made during the detach stage.

In accordance with at least some embodiments, one or more of the private flow line sensors 110A-110N may correspond to micro-electromechanical system (MEMS) sensors. Such MEMS sensors may have a size of 0.1 inches or less and include a processing unit, a memory, and a microsensor. Such MEMS sensors are created, for example, by a deposition process that is normally applied to semiconductor device fabrication.

As one example, a MEMS temperature sensor can determine temperature from infrared signals generated by a fluid sample. Another example MEMS temperature sensor can determine temperature by sensing geometrical changes to at least one object and in associating the changes with temperature. An example MEMS pressure sensor can be based on detection of movement of a membrane that bounds a cavity based on the changes in the volume of material in the cavity with changing pressure. Another example MEMS pressure sensor can be based on a material (e.g., a piezoelectric material) that generates electrical signals when different pressure is applied. An example MEMS resistivity sensor measures the resistivity of the sample. An example MEMS ultrasonic or acoustic transducer measures the acoustic properties of the sample based on reflections. In one embodiment, a MEMS acoustic transducer uses the Doppler Effect to determine flow measurements. Example MEMS chemical sensors may test for concentration of certain materials such as $H_2S$. When placed in the sampling chamber, a protective casing may protect the sensor from corrosion, high-pressure, and high temperature. Due to small size of the sensors, they can be more easily integrated with the private flow line or sample chamber. Further, multiple sensors at different locations around the private flow line or sample chamber can be used to monitor temperature gradients. Due to low power consumption, MEMS sensor can run on a small battery or via an existing power delivery system.

Depending on the application, MEMS sensor measurements and/or other sensor measurements can be accessed downhole or uphole via available telemetry methods. Sensor measurements can be collected during retrieval of a downhole tool and/or while a fluid sample is directed to the sample chamber. Further, sensor measurements can be recorded as a function of time, with sampling frequencies extending up to 500 Hz, and sample lengths extending up to 10 million sample points. As an example, time-sensitive measurements can be viewed manually or can be analyzed by a monitoring algorithm that monitors changes as the sample is being retrieved. The monitoring algorithm can raise different flags in response to measurements or changes to measurements surpassing predetermined thresholds.

The fluid sampling assembly 101 also includes detachable sample chambers 116A-116N for each respective private flow line 107A-107N. In accordance with at least some embodiments, each of the detachable sample chambers 116A-116N includes a movable piston or expandable material responsive to pressure to enable filling the chamber. Each of the detachable sample chambers 116A-116N can be sealed using respective detachment valves 114A-114N, each actuated manually or by a separate control signal CTR_D1 to CTR_DN. Once sealed, each of the detachable sample chambers 116A-116N can be detached from assembly 101 at a respective detachment point 112A-112N.

In operation, the fluid sampling assembly 101 sends uplink data to (e.g., sensor data) and receives downlink data (e.g., commands) from a monitoring/control system 120. The monitoring/control system 120 may correspond to a computer system (e.g., computing facilities 45). Additionally or alternatively, at least part of monitoring/control system 120 may be included with the downhole tool that includes assembly 101. As shown, the system 100 also includes storage system 122 to store uplink data for later processing and/or analysis. To distinguish between communications to or from different components of the assembly 101, the system 100 may employ an addressing or tagging scheme. For example, each of the private flow lines 107A-107N may have at least one respective tagging components 111A-111N to tag measurements from private line sensors 110A-110N. In at least some embodiments, the tagging components 111A-111N add a unique chamber identifier to measurements. Further, system 100 may include an uplink interface 109 to prepare uplink data packets with suitable fields. As an example, an uplink data packet may include a unique chamber identifier field, a sensor type field, and a measurement value field. In this manner, sensor measurements may be later associated later with a particular detachable sample chamber.

In at least some embodiments, the private line sensors 110A-110N include or are in communication with a wireless interface such as a radio-frequency identification (RFID) interface, a Bluetooth® interface, an infrared light interface, or a laser interface that adds the unique chamber identifier to collected measurements. Such wireless interfaces may simplify the design of assembly 101, but are not required. Regardless of how the unique chamber identifiers are associated with sensor measurements, the uplink interface 109 is able to receive, buffer, and prepare measurement data from multiple sensors and to generate uplink data packets that preserve the information regarding the unique chamber identifier, the sensor measurement value, and the sensor type for each measurement.

Figure 3A:
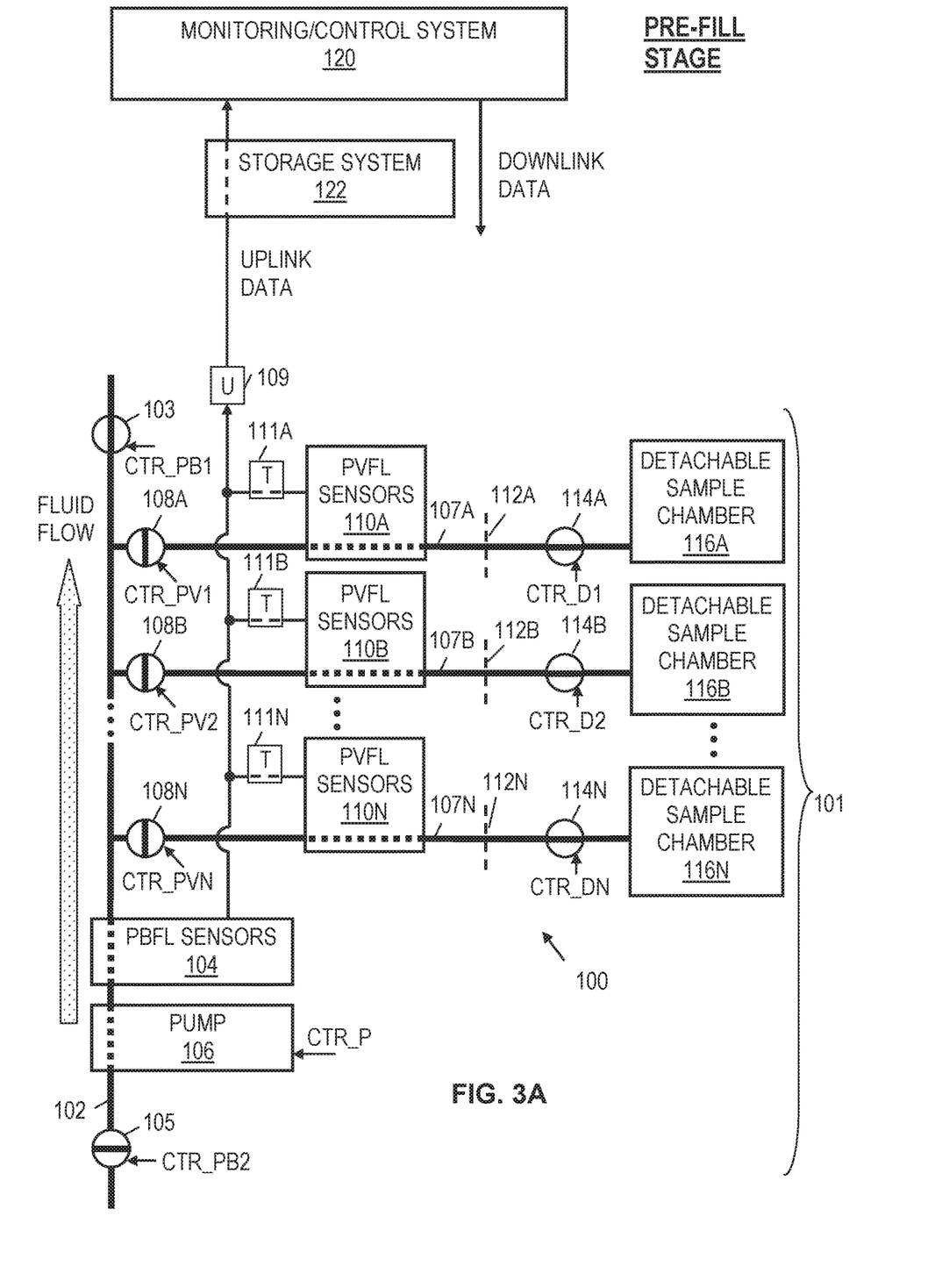
FIG. 3A-3D show an illustrative formation fluid sampling system during various stages of a fluid sampling process.

FIG. 3A corresponds to a pre-fill stage for system 100. During the pre-fill stage, formation fluid is drawn into the public flow line 102 by opening valve 105 and actuating pump 106. To direct formation fluid out of the public flow line 102, the valve 105 is closed, the valve 103 is opened, and the pump 106 is again actuated. The pre-fill stage operations for valves 105 and 103, and pump 106 can be performed using control signals CTR_PB2, CTR_PB1, and CTR_P. The process of drawing formation fluid into public flow line 102 and directing the formation fluid out of the public flow line 102 may continue until measurements collected by the public flow line sensors 104 indicate a quality of the formation fluid is greater than a threshold level. For example, the threshold level may correspond to a predetermined purity level and/or the absence of contaminants, particles, borehole fluids, etc. If a quality sample cannot be obtained, the pre-fill stage operations can be repeated with adjustments made to the position of the downhole tool and/or the position of an arm or tool extension that contacts the borehole wall to draw fluid therefrom.

Figure 3B:
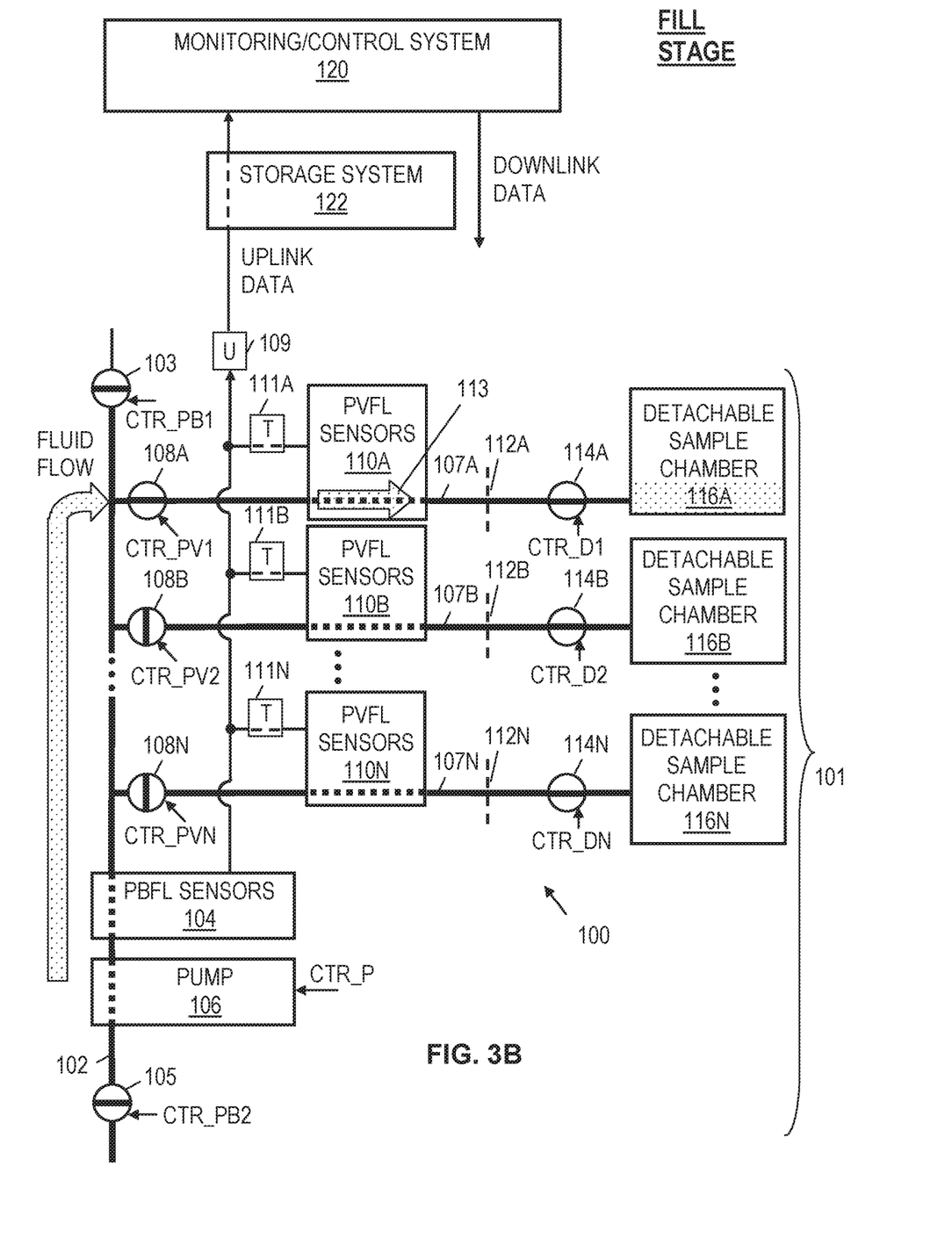

After the pre-fill stage obtains suitable formation fluid, a fill stage represented by FIG. 3B begins. More specifically, the fill stage of FIG. 3B fills detachable sample chamber 116A. In the fill stage, valves 103 and 105 are closed with formation fluid remaining in the public flow line 102. Subsequently, isolation valve 108A is opened and pump 106 is actuated to direct formation fluid through private flow line 107A, through detachment valve 114A, and into detachable sample chamber 116A. If more fluid is needed to fill the detachable sample chamber 116A, the isolation valve 108A is closed, and valves 103, 105, and pump 106 are actuated to re-fill the public flow line 102 as previously described. Thereafter, valves 103 and 105 are closed with formation fluid remaining in the public flow line 102, isolation valve 108A is opened, and pump 106 is actuated to direct more formation fluid through private flow line 107A, through detachment valve 114A, and into detachable sample chamber 116A. This fill process can be repeated as needed, and the fill stage operations for valves 105 and 103, isolation valve 108A, and pump 106 can be performed using control signals CTR_PB2, CTR_PB1, CTR_PV1, and CTR_P. In at least some embodiments, the function of valves 103 and/or 105 is integrated in the pump 106 by sample check valves. The pump can draw in fluid from one port (upstream) and pump out to a different port (downstream), where the upstream and downstream are isolated by check valves.

As the formation fluid flows through private flow line 107A, private line sensors 110A measure properties of the formation fluid. To represent such measurements private line fluid 113 is shown passing through the private flow line sensors 110A. Such measurements may correspond to temperature, pressure, chemical presence/concentration, electromagnetic properties, resistivity, acoustic properties, and/or $H_2S$ presence/concentration.

Although FIG. 3B describes operations for filling detachable sample chamber 116A, it should be understood that similar operations could be used to fill the other detachable sample chambers 116B-116N one at a time. For example, in at least some embodiments, the fill stage includes taking fluid samples at a plurality of depths. For each depth, a different one of the detachable sample chambers 116A-116N is filled. Accordingly, the uplink communication protocol employed by the uplink interface 109 may include a depth data field to record the depth associated with a fluid sample. Once the fill stage operators are complete, the isolation valves 108A-108N are closed to isolate the private flow line 107A-107N and the detachable sample chambers 116A-116N from the public flow line 102. The fill stage operations for valves 105 and 103, isolation valve 108A, and pump 106 can be performed using control signals CTR_PB2, CTR_PB1, CTR_PV1, and CTR_P.

Figure 3C:
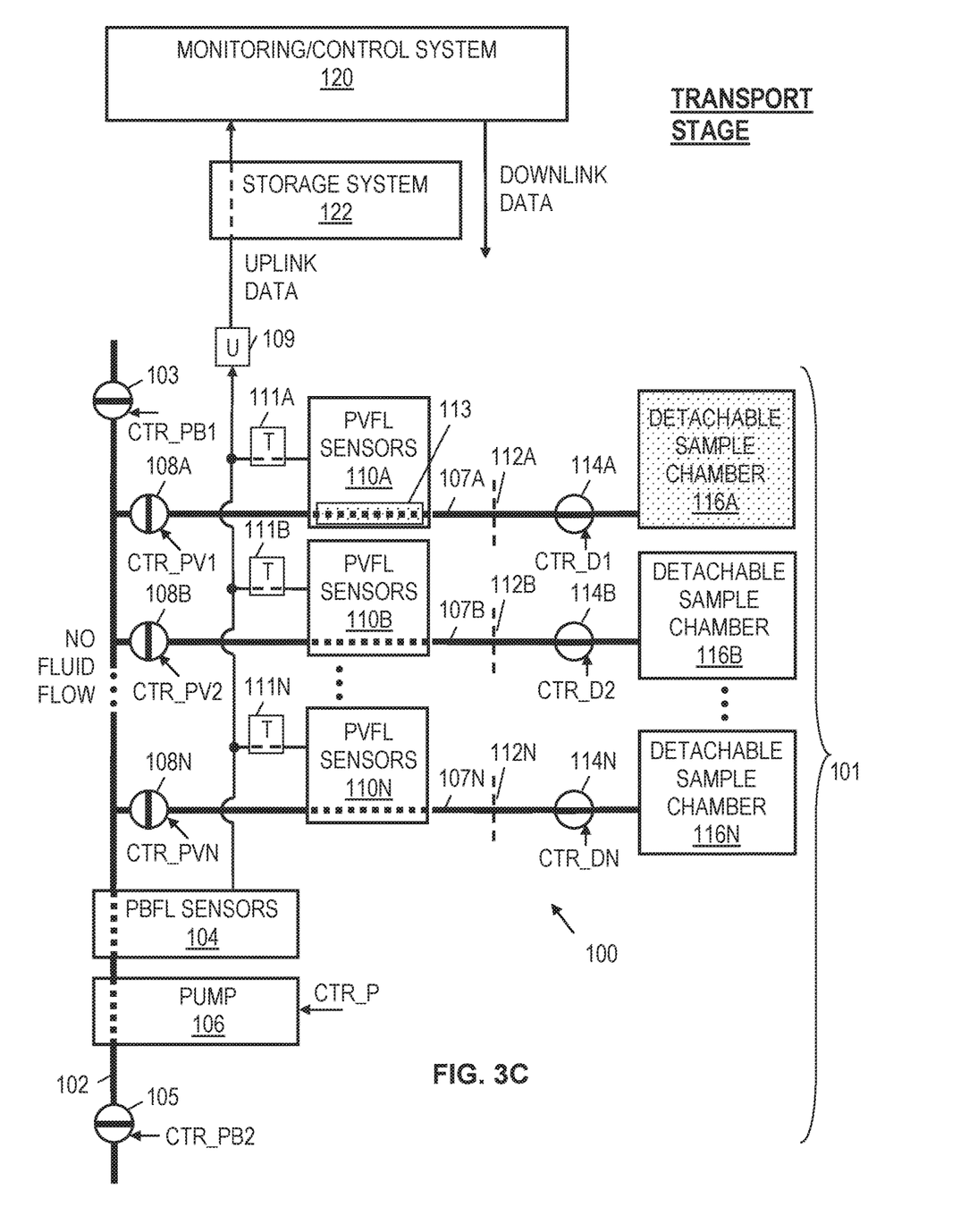

After the fill stage is complete, a transport stage represented by FIG. 3C begins in the transport stage, the fluid sampling assembly 101 with sealed/isolated private flow lines 107A-107N is transported towards earth's surface. For example, a downhole tool (e.g., tool 28) with assembly 101 may be raised towards earth's surface as a related drill string (e.g., drill string 8) or cable (e.g., cable 42) is raised. During the transport stage, private flow line sensors 110A monitor private line fluid 113. Such measurements may indicate temperature, pressure, chemical presence/concentration, electromagnetic properties, fluid density, dielectric strength, resistivity, acoustic properties, and/or $H_2S$ presence/concentration.

In at least some embodiments, the monitoring/control system 120 receives measurements from the private line sensors 110A-110N associated with private flow lines or detachable sample chambers that are in use. Such measurements may be received, for example, during the fill stage and/or transport stage. As needed, the monitoring/control system 120 initiates replacement sample operations in response to measurements that indicate a problem such as an isolation valve leak, a detachable sample chamber leak, contamination, and/or an unsuitable sample. The replacement sample operations may involve the same detachable sample chamber or another detachable sample chamber, and are preferably initiated while fluid sampling assembly 101 is still below earth's surface. In other words, monitoring measurements from private line sensors 110A-110N occurs in real-time or near real-time, and is used to determine whether replacement sample operations are needed before the fluid sampling assembly 101 reaches the earth's surface. The replacement sample operations are preferably conducted at or near the same depth as the sample being replaced.

Figure 3D:
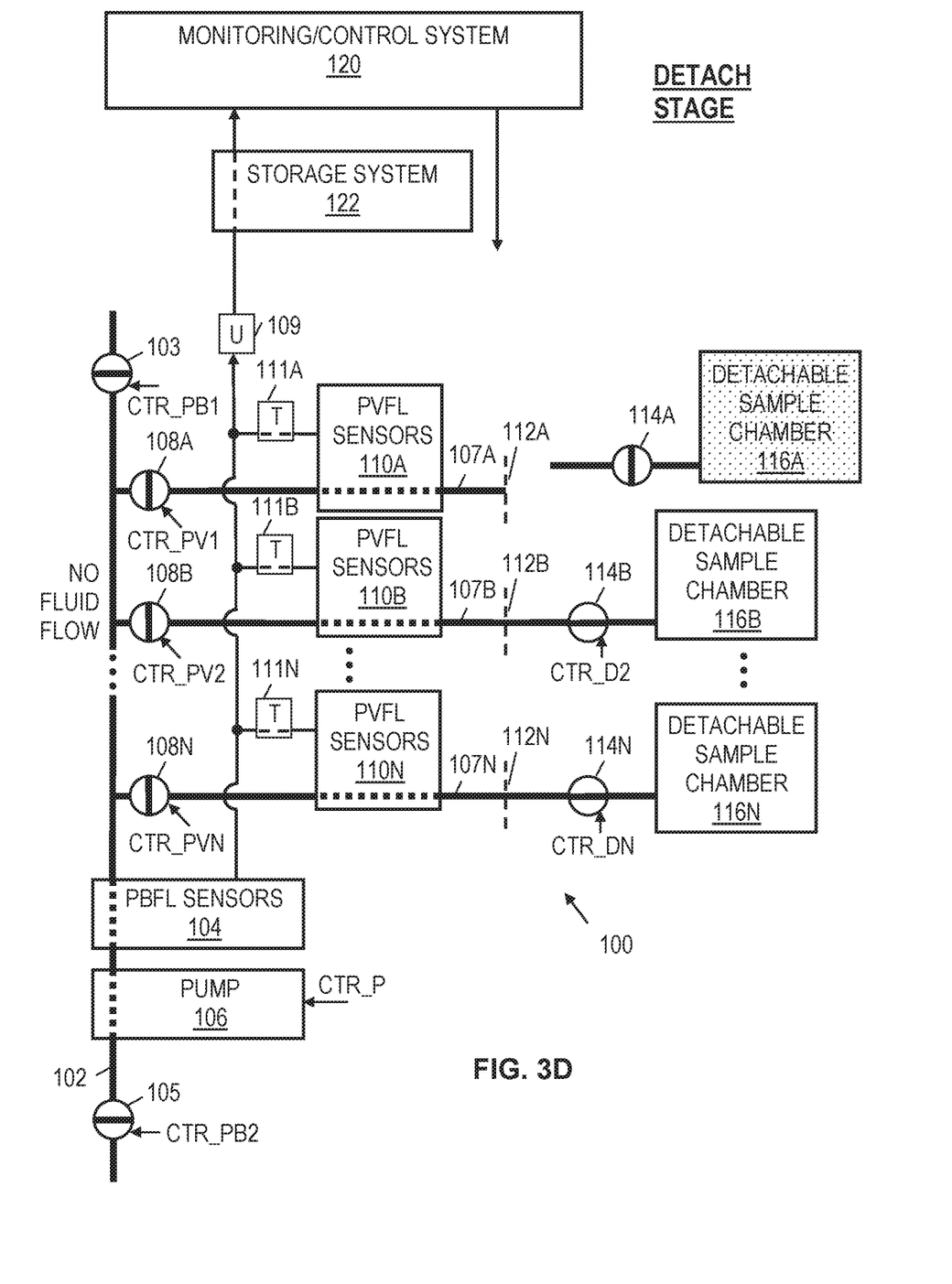

Once the fluid sampling assembly 101 reaches earth's surface, a detach stage represented by FIG. 3D begins. In the detach stage, a detach valve 114A for the detachable sample chamber 116A is actuated to seal the fluid content of the detachable sample chamber 116A inside. Once sealed, the detachable sample chamber 116A is separated from assembly 101 at detachment point 112A. The detachable sample chamber 116A can then be sent to a formation fluid analysis station or laboratory. Further, measurements collected from private flow line sensors 110A during the fill stage and/or the transport stage may be provided to the formation fluid analysis station or laboratory. In at least some embodiments, such measurements are tagged with a unique identifier by tagging component 111A for later association with the detachable sample chamber 116A at the formation fluid analysis station or laboratory. If multiple detachable sample chambers are used, the tagging operations enable a computing system and/or operator to distinguish between measurements associated with different detachable sample chambers. Although FIG. 3D describes detach stage operations for detachable sample chamber 116A, it should be understood that similar operations apply to the other detachable sample chambers 116B-116N. The detach stage operations for detach valves 114A-144N can be performed by manually adjusting detach valves 114A-114N.

Figure 4:
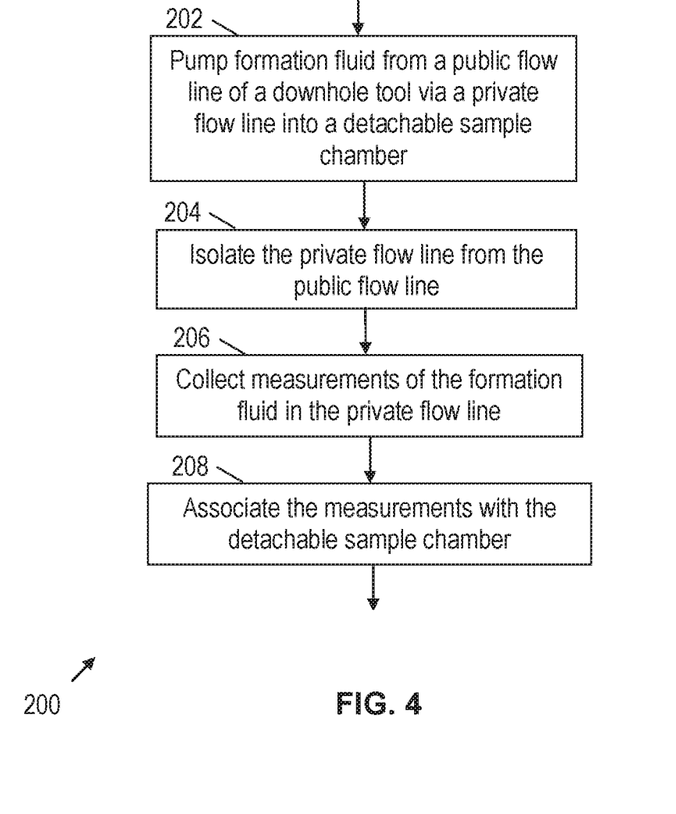
FIG. 4 shows a flowchart of an illustrative formation fluid sampling method.

FIG. 4 shows a flowchart of an illustrative fluid sampling method 200. The method 200 may be performed by a downhole tool (e.g., downhole tool 28), a fluid sampling assembly (e.g., assembly 101), and/or computing facilities (e.g., facilities 45). As shown, the method 200 includes pumping formation fluid from a public flow line of a downhole tool via a private flow line into a detachable sample chamber (block 202). At block 204, the private flow line is isolated from the public flow line. For example, an isolation valve between the private flow line and the public flow line may be actuated to provide the isolation. At block 206, measurements of the formation fluid in the private flow line are collected. Such measurements may be collected, for example, during the pumping operations of block 202 and/or after isolating the private flow line from the public flow line at block 204. Further, the measurements collected at block 206 may correspond to sensor data collected as the downhole tool is raised towards earth's surface, with associated reductions in temperature and pressure. Without limitation, example measurements include temperature, pressure, and $H_2S$ concentration. The collected measurements are associated with the detachable sample chamber at block 208. For example, collected measurements may be associated with the detachable sample chamber using a unique identifier assigned to the detachable sample chamber. To associate collected measurements with a particular detachable sample chamber, tagging operations using the detachable sample chamber's unique identifier are performed. As an example, unique identifiers may be assigned using silicon identification integrated circuits (SIDs).

In at least some embodiments, the method 200 additionally or alternatively includes other steps. For example, the method 200 may include the step of sealing the detachable sample chamber to isolate the detachable sample chamber from the private flow line and detaching the detachable sample chamber from the downhole tool. Further, the method 200 may include the step of transporting the detachable sample chamber to a formation fluid analysis station, retrieving the measurements from the tool, and communicating the measurements to the formation fluid analysis station.

In at least some embodiments, the method 200 includes the steps of pumping, isolating, and collecting for a plurality of detachable sample chambers, each detachable sample chamber being connected to the public flow line by a respective private flow line. Further, the method 200 may include initiating a replacement sample process using the detachable sample chamber in response to analysis of the measurements while the downhole tool is below earth's surface. Further, the method 200 may include initiating a replacement sample process using another detachable sample chamber in response to analysis of the measurements while the downhole tool is below earth's surface.

Embodiments disclosed herein include:

A: A formation fluid sampling method that comprises pumping formation fluid from a public flow line of a downhole tool via a private flow line into a detachable sample chamber, isolating the private flow line from the public flow line, collecting measurements of the formation fluid in the private flow line, and associating the measurements with the detachable sample chamber.

B: A downhole tool that comprises a public flow line with a pump; a detachable sample chamber, the detachable sample chamber being connected to the public flow line via a private flow line with a controllable valve; a controller that directs the controllable valve to open during a fill operation in which the pump directs formation fluid into the detachable sample chamber; and a set of one or more sensors along the private flow line to collect measurements during or after the fill operation, wherein the measurements are associated with the detachable sample chamber.

Each of the embodiments, A and B, may have one or more of the following additional elements in any combination: Element 1: sealing the detachable sample chamber to isolate the detachable sample chamber from the private flow line, detaching the detachable sample chamber from the downhole tool, transporting the detachable sample chamber to a formation fluid analysis station, retrieving the measurements from the tool, and communicating the measurements to the formation fluid analysis station. Element 2: further comprising performing said pumping, isolating, and collecting operations for a plurality of detachable sample chambers, each detachable sample chamber being connected to the public flow line by a respective private flow line. Element 3: each detachable sample chamber has a unique identifier, and wherein said associating operation includes tagging the measurements with the unique identifier for the corresponding sample chamber. Element 4: the measurements include sensor data collected during the pumping operation. Element 5: the measurements include sensor data collected after isolating the private flow line from the public flow line. Element 6: the measurements include sensor data collected as the downhole tool is raised towards earth's surface, with associated reductions in temperature and pressure. Element 7: the measurements include $H_2S$ concentration. Element 8: the measurements include pressure. Element 9: further comprising initiating a replacement sample process using the detachable sample chamber in response to analysis of the measurements while the downhole tool is below earth's surface. Element 10: further comprising initiating a replacement sample process using another detachable sample chamber in response to analysis of the measurements while the downhole tool is below earth's surface.

Element 11: the set of sensors is positioned between the controllable valve and a chamber detachment point of the private flow line. Element 12: further comprising at least one additional detachable sample chamber and a tagging component to tag collected sensor data associated with different detachable sample chambers with a unique identifier. Element 13: the tagging component comprises a wireless transmitter. Element 14: further comprising public flow line sensors, wherein the controller initiates the fill operation in response to the public flow line sensors indicating that formation fluid in the public flow line has reached a threshold quality. Element 15: the set of sensors include micro-electromechanical system (MEMS) temperature or pressure sensors. Element 16: the set of sensors include micro-electromechanical system (MEMS) resistivity sensors. Element 17: the set of sensors include micro-electromechanical system (MEMS) acoustic sensors. Element 18: the set of sensors include micro-electromechanical system (MEMS) chemical sensors. Element 19: the controller initiates a replacement sample process using the detachable sample chamber in response to analysis of the measurements while the downhole tool is below earth's surface. Element 20: the controller initiates a replacement sample process using another detachable sample chamber in response to real-time analysis of the measurements while the downhole tool is below earth's surface. Element 21: the measurements include $H_2S$ concentration and pressure.

Numerous other modifications, equivalents, and alternatives, will become apparent to those skilled in the art once the above disclosure is fully appreciated. It is intended that the following claims be interpreted to embrace all such modifications, equivalents, and alternatives where applicable.

What is claimed is:

1. A downhole tool, comprising:
   a public flow line with a pump;
   a detachable sample chamber having a detachment valve, the detachable sample chamber being connected to the public flow line via a private flow line of the downhole tool with a controllable valve of the downhole tool;
   a monitoring/control system that directs the controllable valve and the detachment valve to open during a fill operation in which the pump directs fluid through the public flow line and the private flow line into the detachable sample chamber;
   public flow line sensors, wherein the controller is configured to initiate the fill operation in response to the public flow line sensors determining that a purity of the fluid in the public flow line has reached a threshold level where borehole fluid is a detectable contaminant that is acceptable up to predetermined trace levels, wherein chemical analysis, particle analysis, or other analysis is employed in the determining; and
   a set of one or more sensors along the private flow line after the controllable valve and before the detachment valve to collect measurements during or after the fill operation.

2. The downhole tool of claim 1, wherein the set of sensors is positioned between the controllable valve and a chamber detachment point of the private flow line.

3. The downhole tool of claim 1, further comprising at least one additional detachable sample chamber and a tagging component to tag collected sensor data associated with different detachable sample chambers with a unique identifier.

4. The downhole tool of claim 3, wherein the tagging component comprises a wireless transmitter.

5. The downhole tool of claim 1, wherein the set of sensors include micro-electromechanical system (MEMS) temperature or pressure sensors.

6. The downhole tool of claim 1, wherein the set of sensors include micro-electromechanical system (MEMS) resistivity sensors.

7. The downhole tool of claim 1, wherein the set of sensors include micro-electromechanical system (MEMS) acoustic sensors.

8. The downhole tool of claim 1, wherein the set of sensors include micro-electromechanical system (MEMS) chemical sensors.

9. The downhole tool of claim 1, wherein the controller initiates a replacement sample process using the detachable sample chamber in response to analysis of the measurements while the downhole tool is below earth's surface.

10. The downhole tool of claim 1, wherein the controller initiates a replacement sample process using another detachable sample chamber in response to real-time analysis of the measurements while the downhole tool is below earth's surface.

11. The downhole tool of claim 1, wherein the measurements include H2S concentration and pressure.

* * * * *